United States Patent [19]
Odland

[11] Patent Number: 6,030,358
[45] Date of Patent: Feb. 29, 2000

[54] MICROCATHETER AND METHOD FOR SITE SPECIFIC THERAPY

[76] Inventor: Rick Matthew Odland, 433 S. Owasso Blvd., Roseville, Minn. 55113

[21] Appl. No.: 08/908,555

[22] Filed: Aug. 8, 1997

[51] Int. Cl.[7] .................................................. A61M 1/00
[52] U.S. Cl. ............................ 604/27; 604/29; 604/43; 604/264
[58] Field of Search ............................ 604/93, 264, 280, 604/27, 28, 48, 49, 53, 19, 43; 128/632, 768

[56] References Cited

U.S. PATENT DOCUMENTS

| | | |
|---|---|---|
| 4,378,797 | 4/1983 | Osterholm et al. . |
| 4,445,500 | 5/1984 | Osterholm . |
| 4,445,886 | 5/1984 | Osterholm . |
| 4,758,431 | 7/1988 | Osterholm . |
| 4,777,953 | 10/1988 | Ash . |
| 4,840,617 | 6/1989 | Osterholm . |
| 4,904,237 | 2/1990 | Janese . |
| 5,002,054 | 3/1991 | Ash et al. . |
| 5,106,365 | 4/1992 | Hernandez . |
| 5,191,900 | 3/1993 | Mishra . |
| 5,200,194 | 4/1993 | Edgren et al. . |
| 5,397,354 | 3/1995 | Wilk et al. . |
| 5,441,481 | 8/1995 | Mishra et al. ............................ 604/29 |
| 5,706,806 | 1/1998 | Kissinger . |
| 5,735,832 | 4/1998 | Karlsson . |
| 5,741,284 | 4/1998 | Karlsson . |
| 5,798,119 | 8/1998 | Herbig et al. . |
| 5,810,760 | 9/1998 | Andrews . |
| 5,810,789 | 9/1998 | Powers et al. ............................ 604/280 |

FOREIGN PATENT DOCUMENTS

WO 98/05369  2/1998  WIPO .

OTHER PUBLICATIONS

C. Onal, et al., Acta Neurochir (Wien) 139:661–669 (1997).
Mori et al., J. Neurotrama 15:30 (1998).
Kanthan et al., J. Neuroscience Meth. 60:151–155 (1995).
Lehman et al., Acta Neurochir.[Suppl.], 67:66–69 (1996).
Hossman, pp. 219–227 in "Dynamics of Brain Edema", Pappius, et al., eds. (1976).
Hatashita, et al., pp. 969–974 in "Intracranial Pressure VII", Hoff et al. eds.
Hoff et al., pp. 295–301 in "Outflow of Cerebrospinal Fluid" (1989).
Waters, et al., "A Comparative Analysis of the Ability of Five Classes of Pharmacological Agents to Augment Skin Flap Survival in Various Modelsand Species: An Attempt to Standardize Skin Flap Research", (Annals of Plastic Surgery. 23(2):117–22, 1989 Aug.)
Yadid et al., "Modified microdialysis probe for sampling extracellular fluid and administering drugs in vivo", Am. J. Physiol. 265:R1205–R1211 (1993).
Linhares et al., Anal. Chem. 64:2831–2835 (1992).
Database WPI, Section PQ, Week 8347, Derwent Publications, Ltd., London, GB; Class P31, AN 83–825588, XP002084971 (Lebedev L I), Feb. 5, 1983.
"A Handbook for Microdialysis and in Vivo Sampling", 1997 Bioanalytical Systems, Inc.
Odland RM, Kizziar R, Rheuark D, Simental A "The Effect of Capillary Ultrafiltration Probes on Skin Flap Edema" Accepted with revisions, Otolaryngology–Head and Neck Surgery.

(List continued on next page.)

*Primary Examiner*—Corrine McDermott
*Assistant Examiner*—Kent Gring

[57] ABSTRACT

An apparatus having a pump reservoir and one or more microcatheters, for use in delivering and/or recovering fluid to and/or from a tissue site or for performing tissue engineering outside of the body. The apparatus can be used in a method to perform site specific microtherapy, including for the treatment of avascular necrosis, compartment syndrome, cerebral edema, and to improve skin flap survival in the course of reconstructive surgery.

21 Claims, 14 Drawing Sheets

OTHER PUBLICATIONS

Odland RM, Umeda A "Therapeutic Tissue Microdialysis: Results of an In Vivo Study" Abstracts of the 16th Midwinter Meeting, Association for Research in Otolaryngology, Feb. 1993.

Odland RM, Sutton RL "Hyperosmosis of Cerebral Injury" Neurological Research. In press.

Goding GS, Odland RM "Skin Flap Physiology" in Cummings C (Ed.): Otolaryngology Head and Neck Surgery, Third Ed., St. Louis, C. V. Mosby Co. 1998. pp. 145–170.

Lonnroth, et al., "A microdialysis method allowing characterization of intercellular water space in humans", Am. J. Physio. 253 (Endocrinol. Metab. 16): E–228–E231, 1987.

Odland, et al., "Reduction of Tissue Edema by Microdialysis", Otolaryngology Head and Neck Surgery, vol. 121, 1995.

Johansen, et al. Pharmacotherapy May 1997; 17(3):464–481, "The Use of Microdialysis in Pharmacokinetics and Pharmacodynamics" (Abstract).

Cimmino et al., Diabetes Metab. Apr. 1997; 23(2):164–170, "Tissue Microdialysis: Practical and Theoretical Aspects" (Abstract).

Odland RM, Cohen JI "Measurement of Interstitial Tissue Compliance in Skin Flaps" Archives of Otolaryngology––Head and Neck Surgery 1988; 114(11):1276–1279. (Abstract).

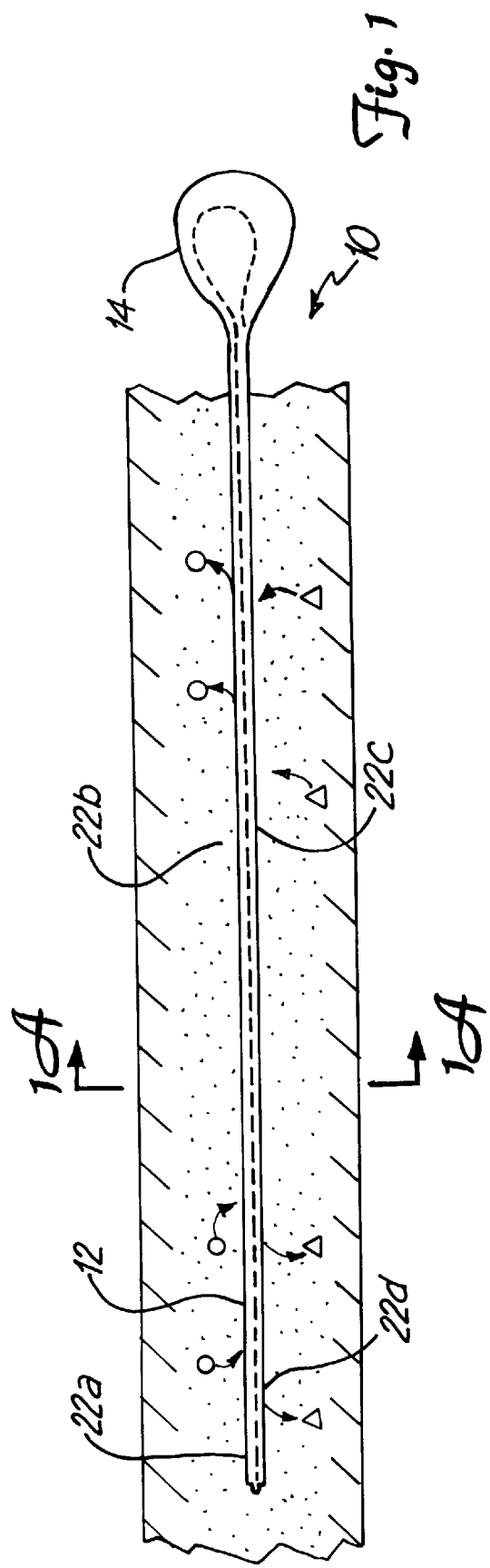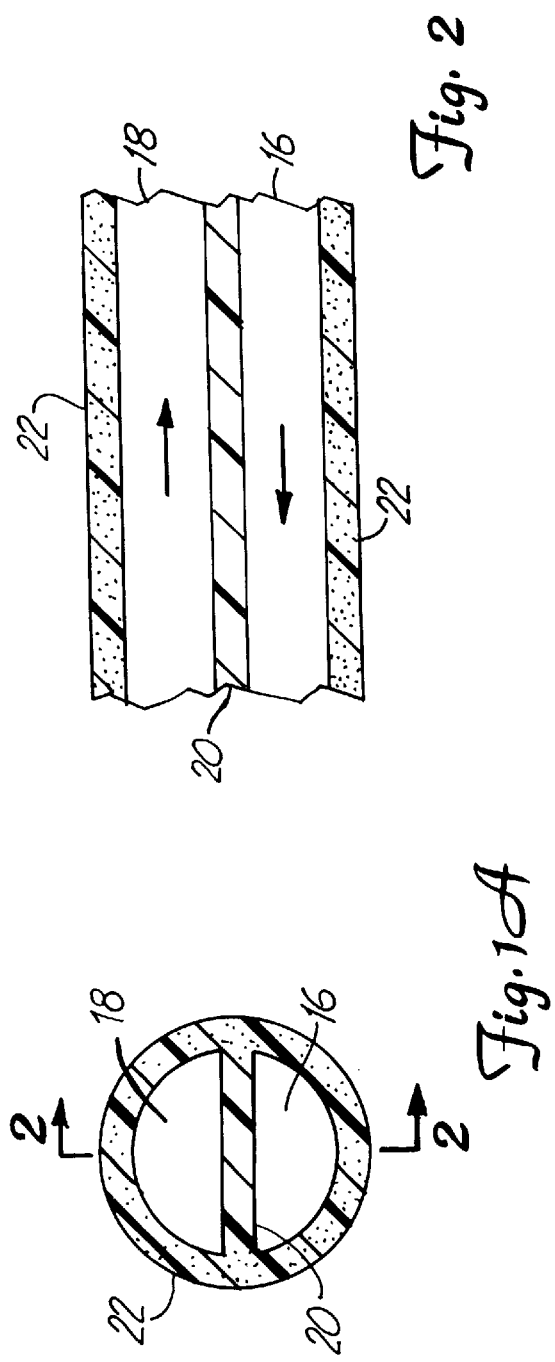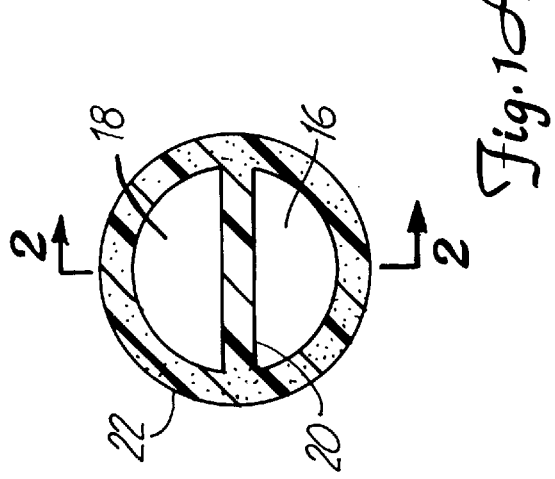

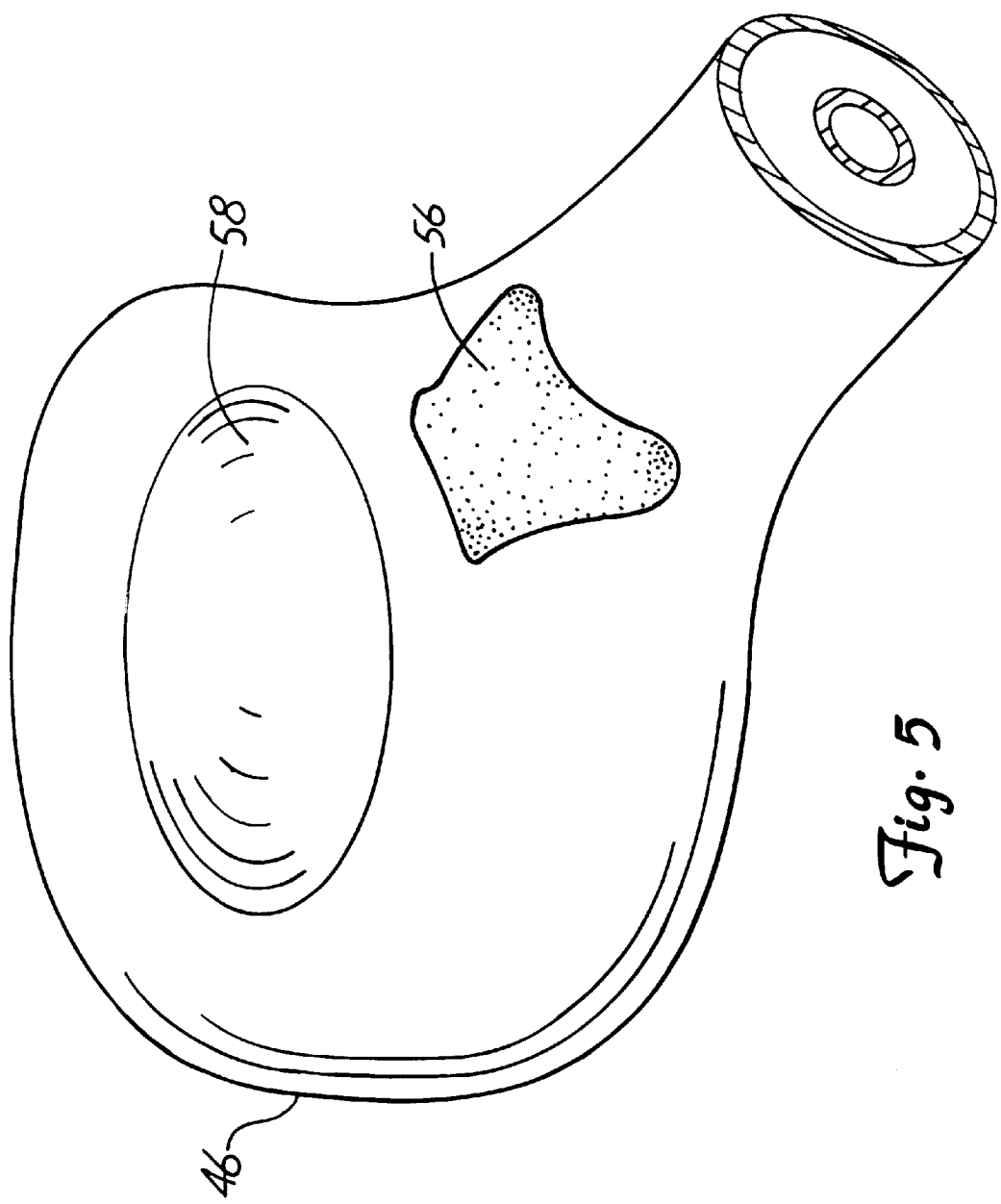

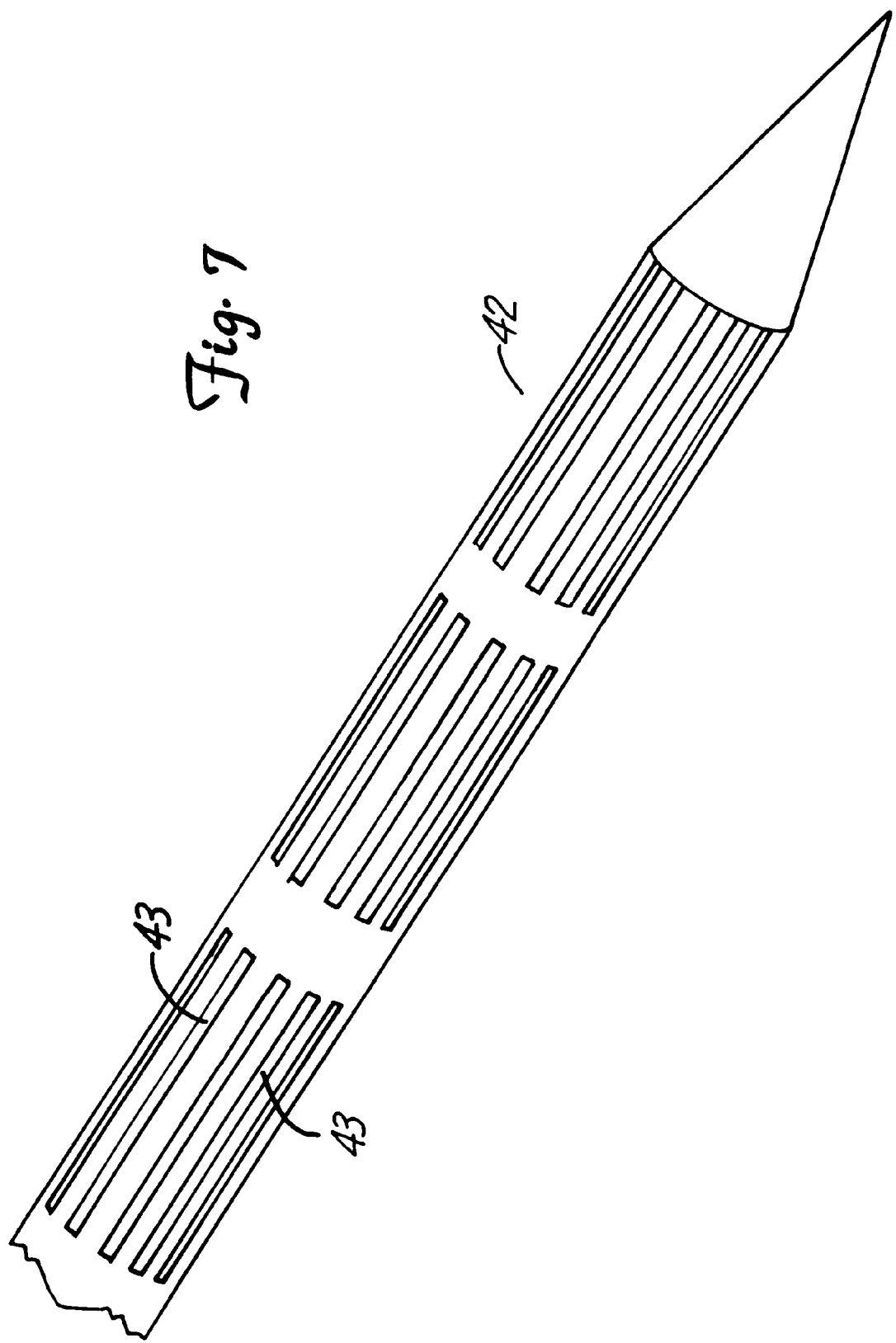

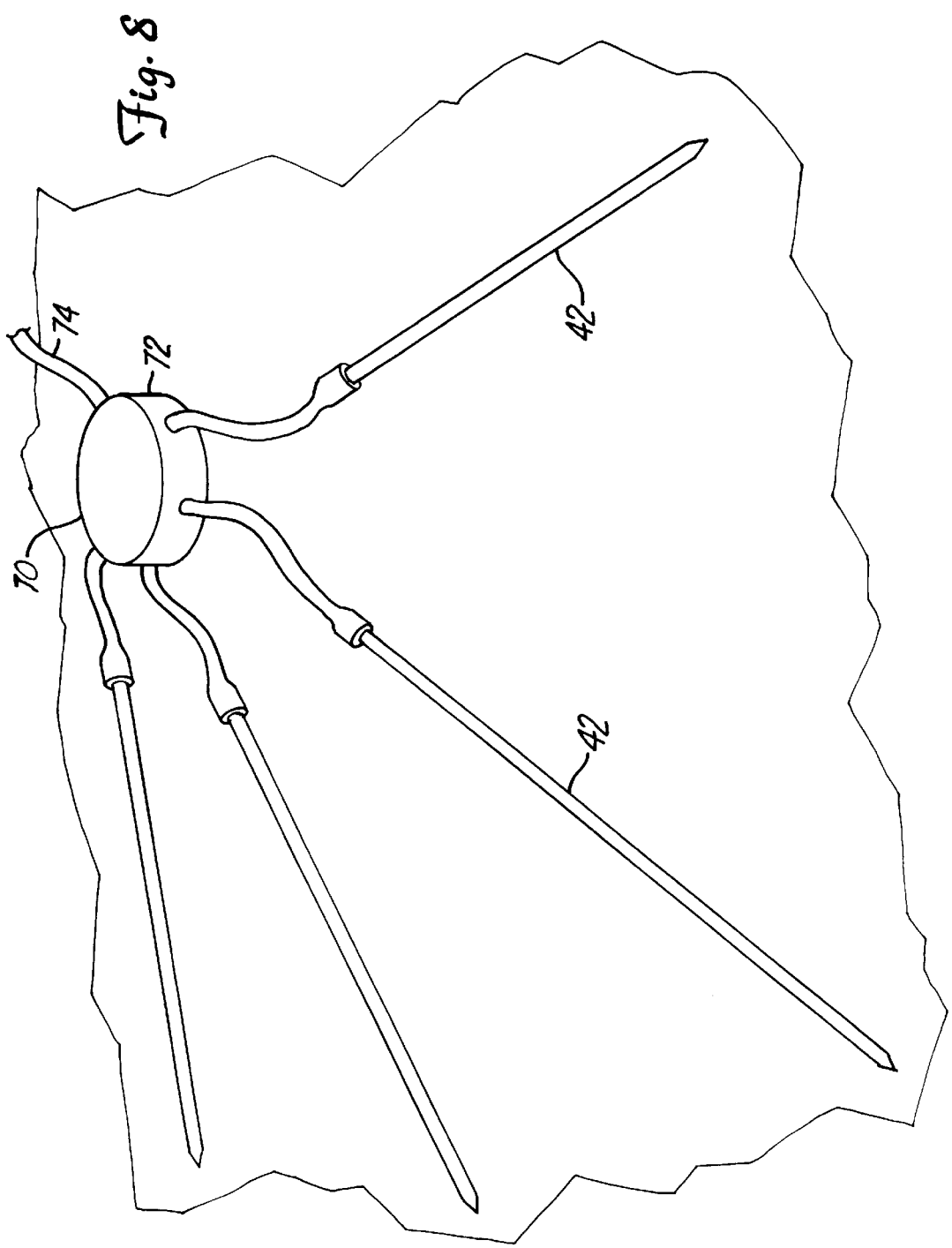

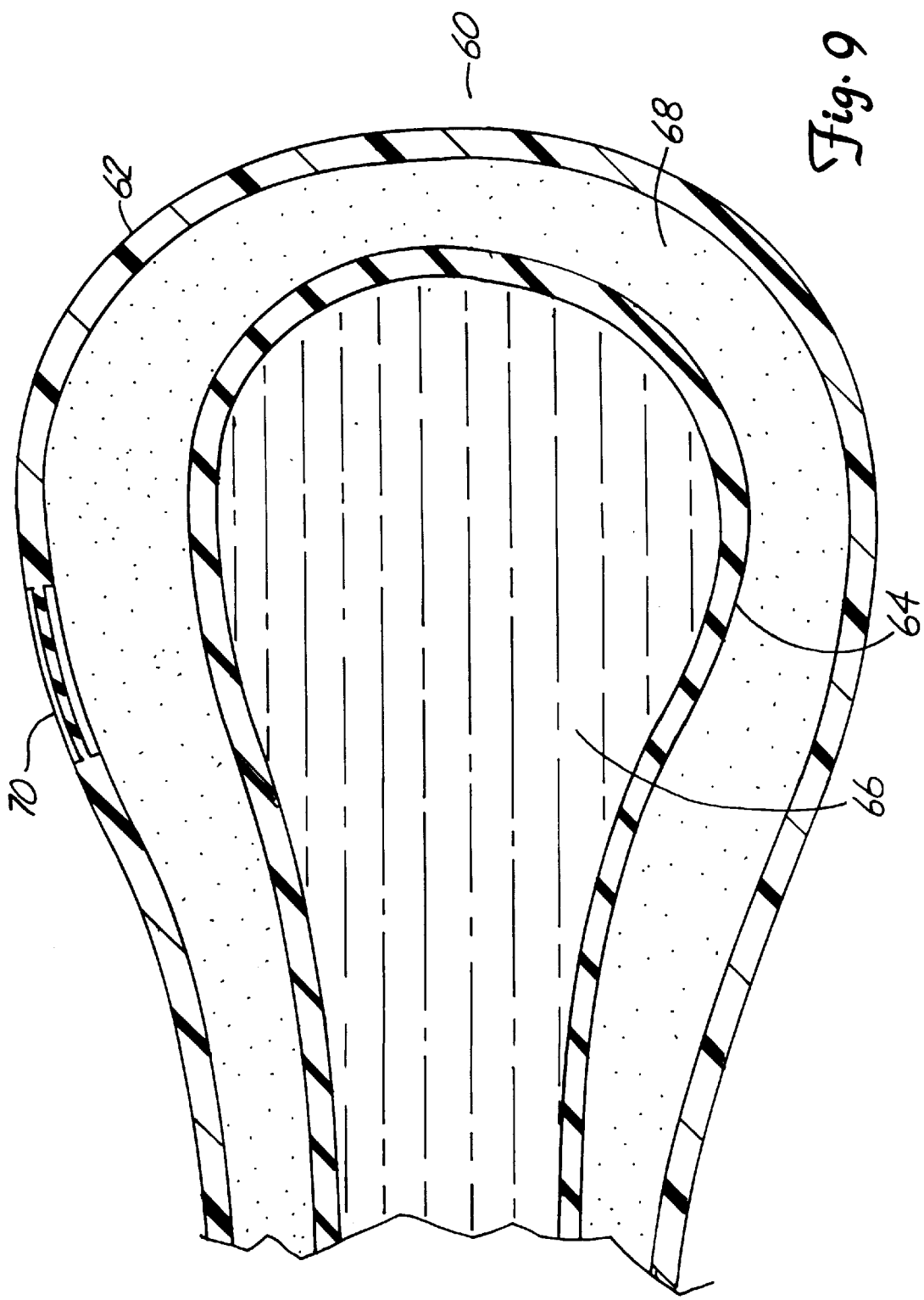

MICROCATHETER AND METHOD FOR SITE SPECIFIC THERAPY

TECHNICAL FIELD

In one aspect, the present invention relates to methods and apparatuses for treating microcirculatory problems, including transient and reversible conditions that do no involve structural injury, as well as permanent or chronic conditions that do involve structural injury to the microcirculation. In another aspect, the invention relates to methods and apparatuses for augmenting normal microcirculation. In a related aspect, the invention relates to methods and apparatuses for treating conditions that involve osteonecrosis, compartment syndrome, edema, and skin flap survival.

BACKGROUND OF THE INVENTION

A number of clinical conditions involve (e.g., are caused by and/or themselves cause) impaired circulation, and particularly circulation within interstitial spaces and within discrete, localized tissues. Among the more vexing examples of such circulatory afflictions are osteonecrosis (e.g., avascular necrosis), compartment syndrome, and edema (and in particular, cerebral edema).

A number of conditions involve poor blood supply to the bone, leading to bone necrosis. Avascular necrosis of the proximal femur, for instance, is the disabling end result of a variety of disease processes that can affect patients of all ages. There is no treatment presently available that can predictably alter the natural history of the disorder. Clinical and radiographic progression to femoral head collapse occurs in approximately 80 percent of cases, and 50 percent undergo total hip replacement within three years. Numerous techniques have been attempted aimed at promoting the early revascularization of the femoral head, with the goal of reversing the usual process ofjoint deterioration. These approaches include muscle pedicle transfer and vascularized bone grafts.

Other methods, including bone remodeling and fracture repair are similar at the cellular level, and involve the coordinated delivery of a variety of cellular elements such as growth factors, such as transforming growth factor beta (TGF-beta), fibroblast growth factor (FGF) and bone morphogenetic protein. Several technical barriers to the treatment of AVN of the femoral head and neck include the limited blood supply of the site, difficult surgical access, and the accelerated progression of the disease due to biomechanical demands of walking on the hip joint.

Acute compartment syndrome generally involves impaired circulation within an enclosed fascial space, leading to increased tissue pressure and necrosis of muscle and nerves. The soft tissue of the lower leg is contained within four compartments, each bounded by heavy fascia—the anterior, lateral, superficial posterior, and deep posterior compartments. The anterior compartment holds the major structures for ankle dorsiflexion and foot and extension. Direct trauma, ischemia, or excessive, unaccustomed exercise can result in hemorrhage and swelling inside the anterior compartment. This swelling will increase pressure on the nerves, veins and arteries inside the compartment. Without arterial circulation, muscle cells will die. In addition, the prolonged compression of nerves can destroy their ability to function.

The neurovascular compression continues to worsen in the following symptoms: weakness or inability to dorsiflex the foot or extend the great toe, decreased ability of the peroneal tendon to evert the foot, and marked itching or prickling sensations in the web between the first and second toe or over the entire dorsal area of the foot. These symptoms must be identified quickly, since misdiagnosis can lead to permanent neuromuscular damage and physical disability.

Diagnosis involves clinical symptoms such as pain and swelling, and signs such as tense compartment pain on passive stretching, parathesia and decreased pulse, and increases in intracompartmental pressure. Once diagnosed, the injury requires immediate decompression through surgical release of the fascia covering the area. Other suggest treatment means include the use of a sympathetic blockade, hyperbaric oxygen therapy, and treatment with mannitol and/or alloperinol.

The characteristics of acute tissue edema are well known, and the condition continues to be a clinical problem, particularly since edema can be detrimental to the tissue as a result of disruption of the microcirculation. Tissue swelling results in increased diffusion distances, which in turn decreases interstitial nutrient delivery. Irreversible disruption of the microcirculatory system can occur as a result of unresolved acute injury. Resolution of tissue edema is problematic since natural mechanisms by which edema resolves are also affected by the edema. Edema compresses venules and lymphatic vessels, and inflammation makes lymphatic vessels hyperpermeable. Pharmacologic treatment is often not effective since blood borne agents have difficulty reaching their target tissue.

Cerebral edema (also known as brain swelling), includes vasogenic cerebral edema (most common form of edema) which manifests itself in the form of increased permeability of small vessels (breakdown of blood-brain barrier) and the escape of proteins and fluids into extracellular space, especially of white matter. Other forms of cerebral edema include cytotoxic cerebral edema (cellular brain edema) and interstitial edema.

Cerebral edema can be caused by ischemia, loss of oxygen, or focal disruption or loss of blood supply such as stroke. In the case of stroke, the specific area must be treated early to prevent further damage. The diagnosis of cerebral edema is based on changes in mental status, imaging, and measurement of intracranial pressure. Conventional treatment of cerebral edema is controversial. Some practictioners insist on keeping the blood pressure high to overcome high intracranial pressure, while others keep the blood pressure low in the hopes of limiting intracranial pressure. Opening the skull generally cannot be done to relieve pressure, because the brain tissue would herniate out the opening causing significant tissue damage. Giving intravenous treatments is also not effective because the brain microcirculation is disrupted so deilivery to the brain is impaired.

The use of skin flaps has gained increased acceptance and use in the course of reconstructive and other forms of surgery. These techniques, however, continue to be plagued by problems having to do with survival of the skin flaps, which in turn, is believed to rely, at least in part, on efficient revascularization of the site. A number of approaches have been considered or evaluated for improving skin flap survival. See, for instance, Waters, et al., which provides a comparative analysis of the ability of five classes of pharmacological agents to augment skin flap survival in various models and species, in an attempt to standardize skin flap research. (Annals of Plastic Surgery. 23(2):117–22, 1989 Aug.).

On a separate subject, the development of methods and apparatuses for tissue microdialysis began at least as early as the early 1960's with the work of Gaddum and others. To date, microdialysis has been used primarily, and with increasing frequency, in the neurosciences, as a means of assaying the interstitial space. In such applications the delivered solution is typically isotonic in order to avoid producing an osmotic gradient and resulting fluid shift. See, generally, Lonroth, et al., *J. Intern. Med.*, 1990 May;227 (5):295–300, "Microdialysis—A Novel Technique for Clinical Investigations"; Johansen, et al. *Pharmacotherapy* 1997 May;17(3): 464–481, "The Use of Microdialysis in Pharmacokinetics and Pharmacodynamics"; and Cimmino et al., *Diabetes Metab.* 1997 April;23(2):164–170, "Tissue Microdialysis: Practical and Theoretical Aspects".

A limited number of references describe the use of microdialysis to deliver substances such at therapeutic agents. Lehmann et al., *Acta Neurochir. Suppl.*, 67:66–69 (1996), describe a microdialysis probe adapted for entry into the parenchyma in order to measure various analytes, the probe being described as useful for possible "therapeutic applications". Similarly, Yadid, et al., *Am. J. Physiol.* 265:R1205–R1211 (1993), describe a modified microdialysis probe for sampling extracelluar fluid and delivering drugs for use in studying the local release and metabolism of neurotransmitters in vivo.

A limited number of other references describe the use of microdialysis to remove interstitial fluid for diagnostic purposes, as described, for instance in Linhares et al., Anal. Chem. 64:2831–2835 (1992). Recent articles have described the use of a hollow fiber catheter to perfuse the catheter with a hypertonic solution in order to intentionally produce a fluid shift and reduce tissue edema. See, for instance, Odland, et al. "Reduction of Tissue Edema by Microdialysis" Arch. Otolaryngol. Head Neck Surg, Vol. 121, pp. 662–666 (1995), which describes the use of a test device having catheters connected by afferent segments of tubing to an infusion pump providing a hypertonic solution of inulin in saline.

To Applicant's knowledge, however, there is no present teaching, let alone clinically acceptable approach for the application of tissue microdialysis in site specific therapy, or in particular, a microdialysis apparatus useful for prolonged periods, difficult sites, and in clinical settings.

SUMMARY OF THE INVENTION

The present application provides an apparatus and method for performing site specific microtherapy, a preferred embodiment of the apparatus comprising one or more microcatheters dimensioned to be positioned within a tissue site, the microcatheter(s) comprising one or more surfaces for delivering fluid to the tissue site and one or more surfaces for removing fluid from the tissue site, the microcatheter(s) being adapted for fluid communication with a pump reservoir for the delivery and/or recovery of fluid. Optionally, and preferably, the apparatus includes such a pump reservoir as a component part.

In a further preferred embodiment, the apparatus provides an outflow circuit for delivering fluid (and/or solutes) to the tissue site and an inflow circuit for removing fluid (and/or solutes) from the tissue site, in combination with a manifold and associated pump system for controlling and directing the flow of fluid within the catheter(s). In one such embodiment, the outflow and inflow circuits each employ one or more catheters to recover and deliver fluid (optionally containing solutes such as biological agents) between sites of healthy and diseased or injured tissue. In another preferred embodiment, the outflow and inflow circuits are provided in the form of separate and substantially parallel recovery and delivery catheters, where they cooperate to provide convective interstitial flow within the tissue site.

Applicant has found that the distribution of fluids within or between portions of a tissue, including the delivery of fluids and any solutes contained therein, can be significantly enhanced by the present apparatus, which can serve to artificially replicate the hydrostatic forces and/or solute delivery characteristics of the microcirculatory system. In such a preferred embodiment the present invention employs microfibril technology to deliver and/or remove fluid, solutes, or specific agents to and/or from a tissue space. In particular, the apparatus permits the infusion of fluids and/or therapeutic agents, and the corresponding removal of tissue fluids and/or biological factors, with the optional ability to simultaneously monitor physiologic parameters. In turn, the invention further provides a commercially viable in vitro tissue engineering technique based on the principle of microdialysis.

The apparatus and method of the present invention can be used for a variety of purposes in the course of providing artificial microcirculation, including for instance, for replicating, repairing, or augmenting circulation inside or outside of the body. In turn, the present invention can be used for a variety of applications, including to treat reperfusion injury or deliver toxic agents directly to a tissue site (inter alia, to avoid systemic toxicity), and for the delivery of poorly diffusible molecules to the interstitum. In particularly preferred embodiments, the apparatus and method of this invention are used to treat clinical conditions that include cerebral edema, stroke, osteoporosis, ischemic osteonecrosis (e.g., avascular necrosis ("AVN") of the femoral head), compartment syndrome, skin flap failure, reperfusion injury, and inflammation in fixed spaces. The apparatus and method of the invention can also be used for the preparation of bone and soft tissue grafts.

A preferred apparatus employs a hydrostatic or osmotic gradient, established by the use of one or more suitably placed and configured catheters, to effect tissue metabolism or fluid flow in large or small sites. The microdialysis system solves the problem of treating focal tissue sites when a) there is inadequate local tissue microcirculatory system to perfuse the tissues, b) systemic toxicity of the agent is a factor, c) the agents to be delivered or removed are large, and d) any combination of the above. The apparatus can be provided as a single catheter, employing either diffusional, osmolar, or hydrostatic forces, or a plurality of catheters having one or more dedicated delivery and recovery catheters, or portions thereof, that employ similar forces.

BRIEF DESCRIPTION OF THE DRAWING

In the Drawing:

FIG. 1 shows a preferred apparatus for the treatment by transdialysis of avascular necrosis, while FIG. 1A shows a cross section of the apparatus.

FIG. 2 shows longitudinal cross section taken along lines 2—2 of the apparatus of FIG. 1.

FIG. 5 shows a perspective view of the pump reservoir of the apparatus of FIG. 4, for use in sampling the interstitial space, while

FIG. 7 shows the delivery sheath depicted in FIG. 4, for use in placing the apparatus.

FIG. 8 shows a manifold for the recovery of interstitial fluids by the use of a plurality of delivery sheaths.

FIG. 9 shows an enlarged view of the pump reservoir for an apparatus of FIG. 4, for therapeutic applications.

DETAILED DESCRIPTION

Figure 3:
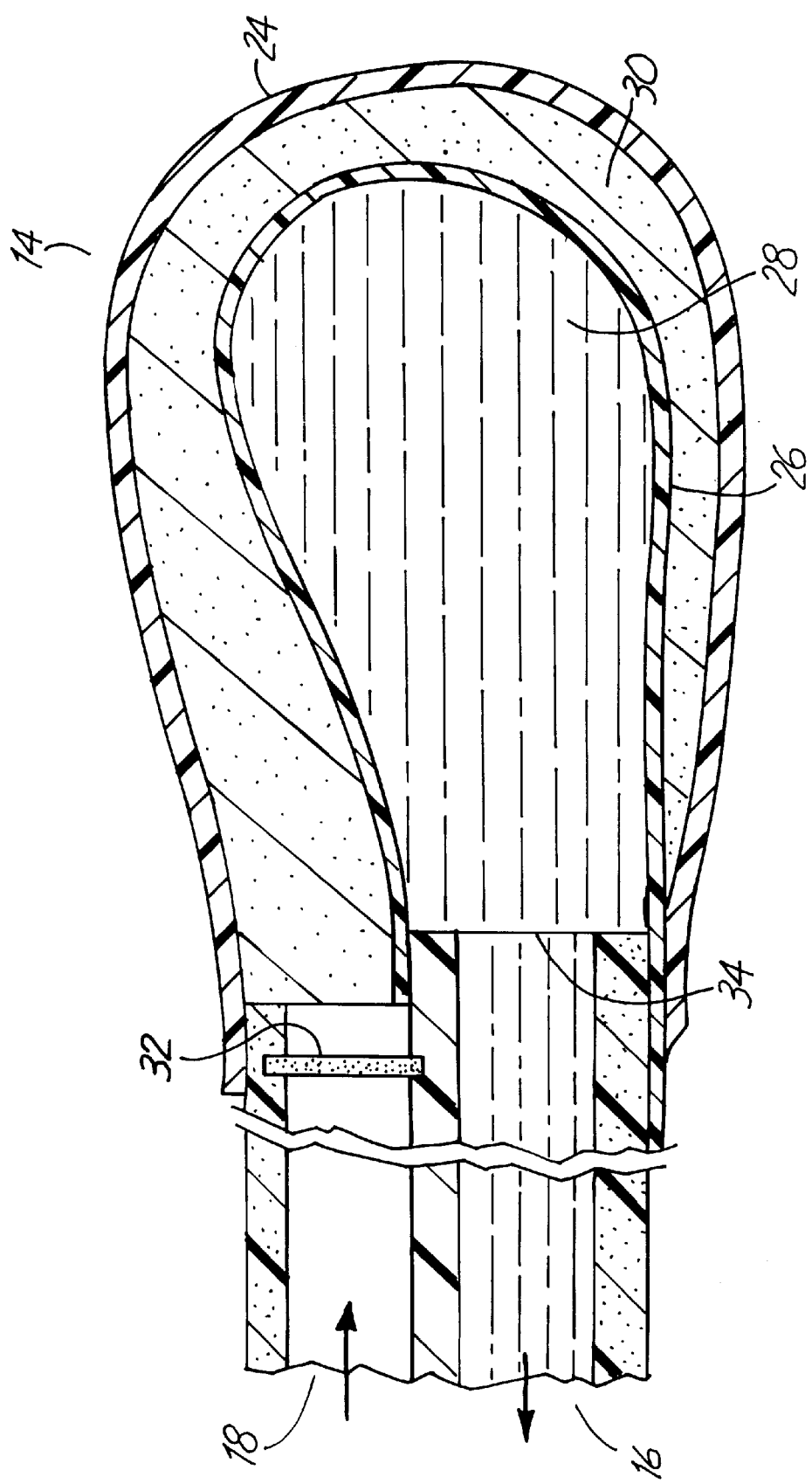
FIG. 3 shows an enlarged cross section of the pump reservoir of the apparatus of FIG. 1.

As used herein, the following terms shall have the meanings ascribed to them below:

The word "apparatus", when applied to the present invention, will refer to a functional combination of a pump reservoir and one or more microcatheters. The word "microcatheter", in turn, will be used to describe a capillary tube having one or more lumen and semipermeable walls or wall portions, while the term "pump reservoir" will refer to the portion(s) of an apparatus that serves to deliver and recover fluid to and from the microcatheter, and in turn to deliver fluid and/or solutes from the tissue site, whether by means of osmolar gradient, hydrostatic pressure, or diffusion, or an appropriate combination thereof. A pump reservoir will preferably have one or more reservoir compartments for holding fluids to be delivered to the microcatheter and one or more reservoir compartments for holding fluids recovered therefrom, in combination with a mechanism for effecting the flow of fluid therebetween.

The word "delivery" will refer to the flow of fluid and/or solutes (e.g., biomolecules) from a pump reservoir and into a lumen of a microcather (and optionally, in turn, into surrounding tissue), while "recovery" will refer to the flow of fluid and/or solutes from a lumen of a microcatheter (on optionally, in turn, from surrounding tissue) and back to the pump reservoir. A microcatheter can be used within an apparatus of this invention for a variety of purposes, including as a microexchange catheter for either delivery or removal. A microcatheter is preferably microporous, e.g., semipermeable or microperforated.

Insofar as the driving forces are concerned, the word "hydrostatic" will refer to fluid dynamics brought about by imposing a positive or negative pressure on a liquid within a microcatheter, as by the application of a microdialysis pump or vacuum, while "hyperosmolar" will refer to fluid dynamics brought about by the use of a solute of sufficient size and concentration within a microcatheter to cause osmotic flow of fluid from surrounding tissue and into, or out of, the microcatheter. In contrast, the word "diffusion" will refer to the spreading or intermixing of materials (fluids and/or solutes), due to molecular movement.

Those skilled in the relevant art, given the present description, will understand the manner in which any suitable combination of hydrostatic, hyperosmolar and diffusional forces can be employed to deliver and recover fluids and/or solutes using microcatheters in the manner provided herein. In general, the method and apparatus of this invention can be used in a site specific manner to achieve any of a number of goals, including to remove excess fluid (and thereby reduce interstitial pressure and improve microcirculation), and to deliver and/or recover agents to or from various parts of the body.

An example of an osmolar (e.g., hyperosmolar) microcatheter apparatus of this invention includes a coaxial microcatheter in which a hyperosmolar perfusate is delivered by hydrostatic (i.e., pressure) means to the distal end of a coaxial microcatheter assembly, whereupon it returns to the pump reservoir together with tissue fluid that is recovered through the semipermeable outer membrane of the assembly by osmosis. Optionally, and preferably, the hyperosmolar perfusate itself contains a sufficiently high concentration of one or more agents to allow the agent to be delivered through the semipermeable membrane and into the tissue by diffusion or other forces. Examples of the use of hydrostatic and diffusion microcatheters include, respectively, the dual catheter and transdialysis embodiments described below.

Osteonecrosis refers to the in situ death of cells within a bone segment, e.g., due to or resulting in a lack of blood flow. The circulation of the femoral head, for instance, is supplied by vessels that pass in a retrograde fashion within the femoral neck. This makes the femoral head particularly vulnerable to AVN from a variety of process that interrupt this blood supply. In infants and children AVN is seen as a consequence of trauma or the treatment of developmental hip dysplasia or slipped capital femoral epiphysis. Spontaneous AVN of the femoral head in children is known as Legg-Calve-Perthes disease. In adults, AVN occurs as the result of trauma or is associated with a variety of disorders including hematologic or autoimmune diseases, corticosteroid therapy, coagulation disorder, alcoholism, barotrauma, and disorders of lipid metabolism.

The invention will be further described with reference to the Drawing, wherein FIGS. 1 through 3 provide an apparatus for treating osteonecrosis that employs different portions of a single catheter to perform transdialysis, in which a patient's own endogenous factors and/or mediators (autologous agents) and other soluble factors are used to promote healing or growth in an affected area. Applicant has discovered, for instance, that early stage AVN can be managed by augmenting current initial treatments (e.g., core decompression) with a apparatus of this invention in order to both reduce interstitial edema and to continuously deliver growth factors. Biological agents can be either endogenous (transdialysis) or exogenous (e.g., delivered by diffusion from within the perfusate).

In particular, the apparatus is designed to employ microcirculation to perform "transdialysis", by the recovery and delivery of factors such as biological mediators and stimulating factors between different portions (e.g., healthy and injured) of the tissue. FIG. 1 shows an apparatus (10) having both a microcatheter component (12) and a delivery pump reservoir (14). The cross sectional and magnified views shown in FIGS. 1A and 2, respectively, show that delivery lumen (16) and recovery lumen (18) are separated by impermeable barrier (20) and surrounded by semipermeable membrane (22). Optionally, the delivery and recovery lumen (in the form of conduits or passageways) can be provided in any suitable form, e.g. in the form of discrete microporous catheters, separated by a barrier to separate and prevent direct contact between the two.

Such an embodiment can be used for a variety of applications, e.g., the repair of necrotic bone brought about by avascular necrosis. As shown in FIG. 1, for instance, the proximal region of bone is healthy bone, while the distal portion is diseased. The microcatheter is positioned within the bone with its distal surfaces in the injured region and its proximal surfaces in healthy bone. Once in place, the surfaces of microcatheter (12) serve a variety of roles, as determined by their location within the tissue (e.g., bone) and along the flow path of delivered fluid. In order, these roles include: a surface (22a) that serves to accumulate and remove biological stimulating factors (identified by o's) from the region of injured bone and transport them to surface 22(b), whereupon the factors are released into healthy bone, where they serve to stimulate the natural production of healing factors (identified by Δ's). The healing factors, in turn, are then accumulated and removed by portion (22c) and carried back into the region of injured bone, where they are themselves able to diffuse out from portion (22d) of the microcatheter surface.

In such an embodiment the delivery and removal functions can be accomplished by any suitable means. Preferably, the delivery function is accomplished by diffusion brought about in the course of hydrostatic flow, while the removal function is accomplished by either hydrostatic or hyperosmolar forces. Optionally, and particularly where both functions (delivery and recovery) are accomplished by hydrostatic forces, the pumps used to produce those forces are separately controllable such that the flow can be balanced or otherwise adjusted between the two, to the point where one or the other pump can be turned off altogether to permit single catheter delivery or removal alone.

FIG. 3 shows a preferred pump configuration for use with the microcatheter of FIG. 1. It can be seen that pump (14) includes both a substantially rigid external bulb (24) and an elastomeric internal bulb (26) containing the fluid (28) to be delivered to the tissue. The fluid can be of any suitable type, e.g., normal saline, Ringer's Lactate, or the like, optionally including medicaments or other therapeutic agents.

A hypertonic solution (30) is positioned in the cavity between external bulb (24) and internal bulb (26), which is retained in position, in part, by a semipermeable barrier (32) positioned between the hypertonic solution (30) and the recovery lumen (18). Optionally, and preferably, a fluid resistor (34) can be positioned between the fluid reservoir and the delivery lumen (16) in order to control flow. In use, fluid (28) is delivered to the microcatheter through lumen (16) by hydrostatic pressure, which initially is caused by osmotic pressure of fluid flowing from recovery lumen (18) and into the chamber containing hypertonic solution (30). More preferably, the apparatus is provided with an activation mechanism to control the onset of flow. In the course of use, the fluid that returns from the microcatheter via lumen (18) enters the space occupied by the hypertonic solution, causing it to swell. This swelling, in turn, further compresses elasomeric bulb (26), resulting in the delivery of additional fluid. The contents of either or both chambers can be provided with external access means (e.g., needle ports) in order replenish or remove their contents, and recharge the apparatus in situ.

An apparatus for the treatment and monitoring of compartment syndrome will be described with reference to the Drawing, wherein FIGS. 4 through 9 show a preferred apparatus (40) for such purposes. Apparatus (40) can itself be provided in a number of optional embodiments, depending for instance on the type of reservoir used, including an embodiment for use in monitoring the site and another embodiment for use in treating the site.

Figure 4:
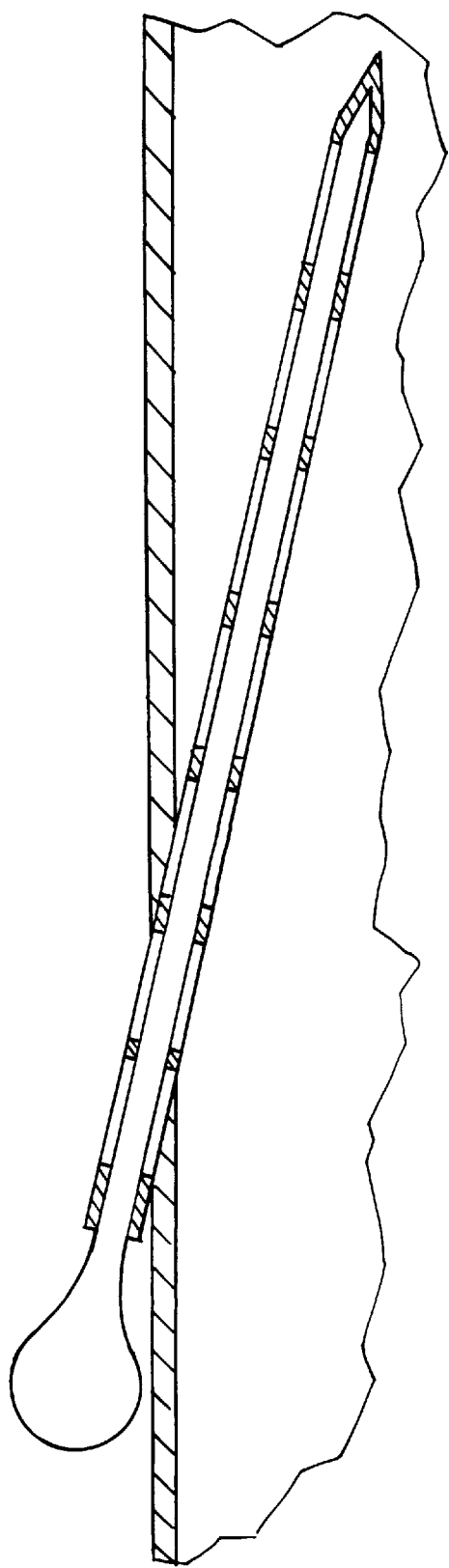
FIG. 4 shows a preferred apparatus for use in monitoring or treating compartment syndrome, including a sheath for its placement.
Figure 6:
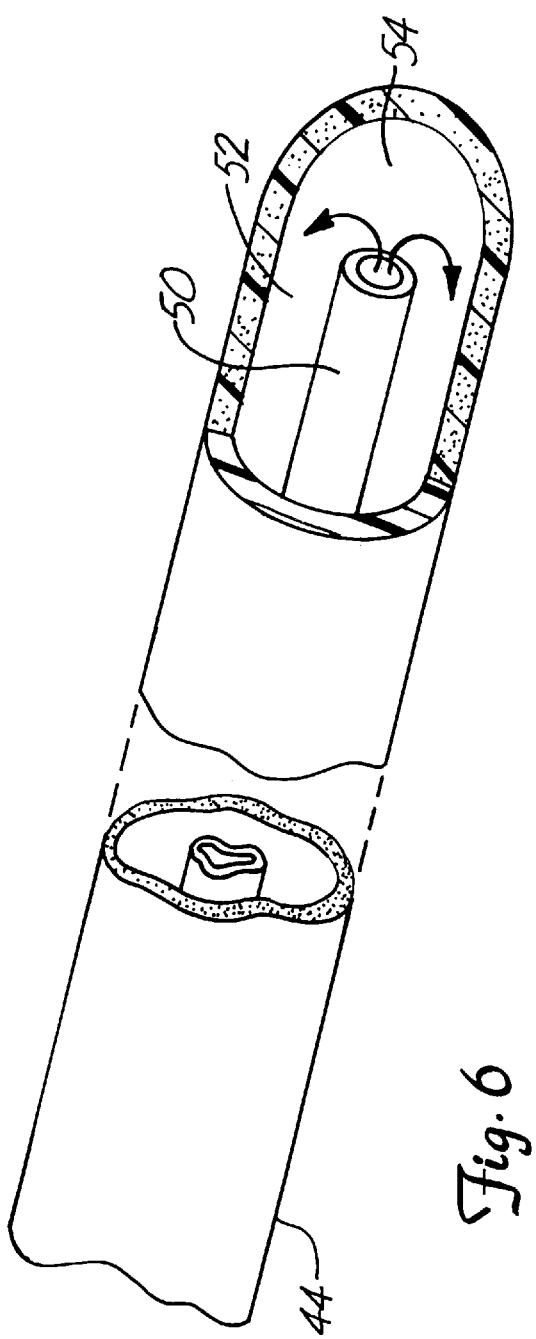
FIG. 6 shows an enlarged view, with portions cut away, of the coaxial microcatheter portion of the apparatus of FIG. 4.
Figure 5A:
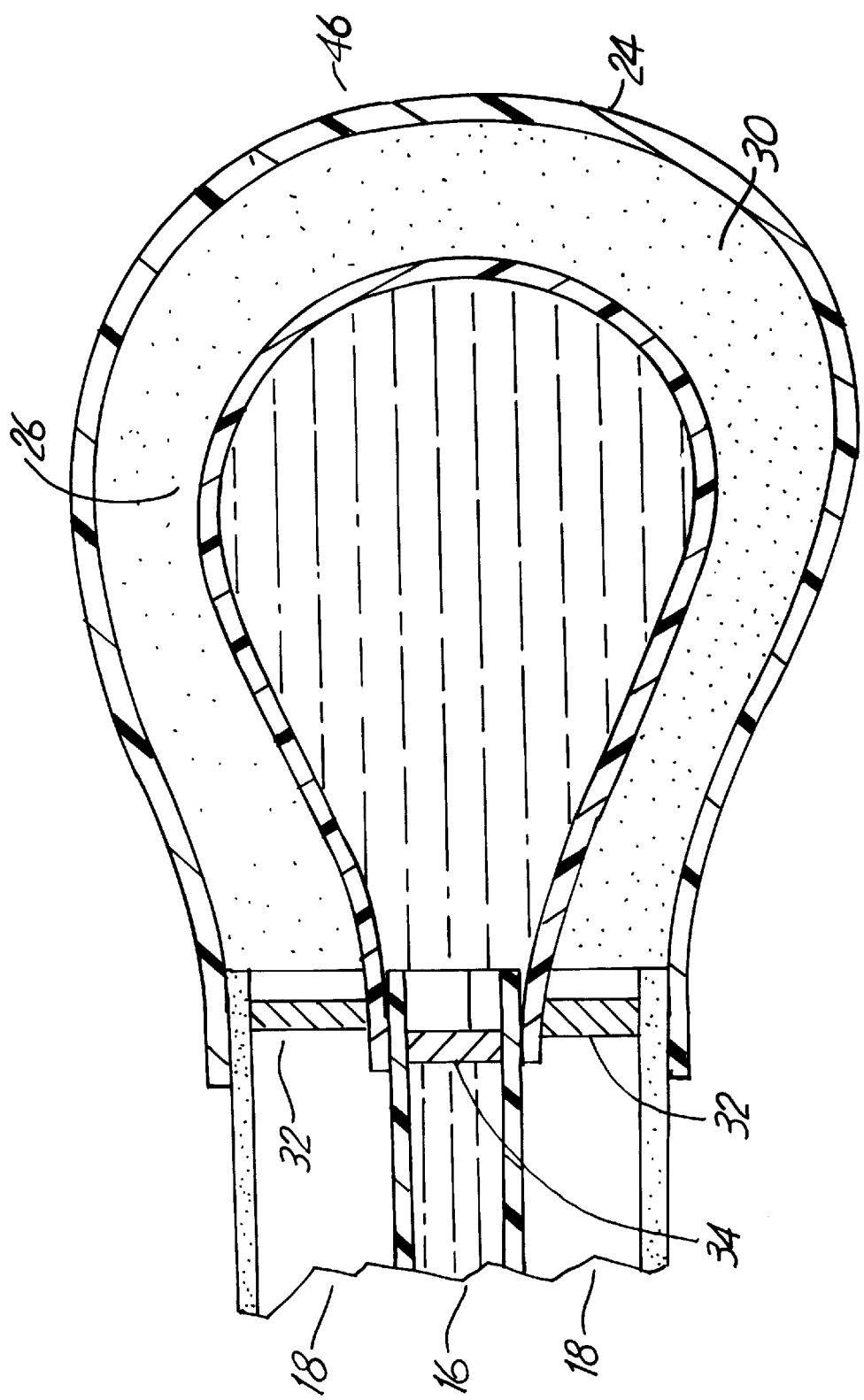
FIG. 5a shows a cross sectional view of the pump reservoir.
Figure 10:
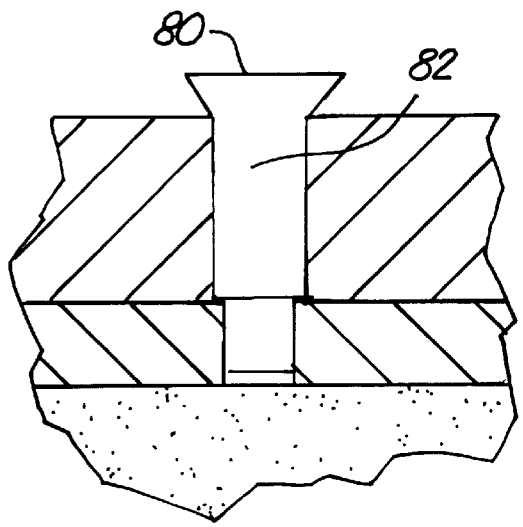
FIG. 10 shows a preferred apparatus for treating cerebral edema.

FIG. 4, in particular, shows an apparatus (40) positioned in place within delivery sheath (42), which in turn is positioned subcutaneously in a site suspected to exhibit compartment syndrome. FIG. 6 shows an exploded view of the microcatheter portion (44) of apparatus (40), while FIGS. 5 and 5A show perspective and cross sectional views, respectively, of a preferred reservoir (46) for monitoring the site. FIG. 7 shows an isolated view of the delivery sheath (42) itself, and FIG. 9 shows a preferred reservoir (60) for treating the site by delivering a hyperosmolar solution to the site. FIG. 8 shows an optional apparatus (70) for use in reducing pressure within the site, that includes a plurality of sheaths as shown in FIG. 7, connected to a manifold and source of negative pressure.

In use, delivery sheath (42) is inserted into a desired position subcutaneously, whereupon the apparatus (40) assembly is inserted into the sheath. As seen in FIG. 7, the sheath is preferably of a size and configuration that will permit it to be inserted into the body, and having walls sufficiently permeable (e.g., as shown having longitudinal grooves (43)) to permit the desired (e.g., uninhibited) flow of fluids within the tissue and between the tissue and microcatheter. With the sheath in position it can be used for a variety of sequential steps, including to first monitor the site in order to diagnose compartment syndrome, and thereafter to treat the site by the reduction of pressure, and optionally, the delivery of medicaments or other agents.

As seen in FIG. 6, a preferred microcatheter (44) for such use is provided in the form of coaxial lumen, including an inner lumen (50) surrounded by an outer lumen (52). Inner lumen (50) is sufficiently shorter than the outer lumen (52) in order to provide for fluid communication between the two lumen at the distal end chamber (54). Inner lumen (50) is preferably formed of an impermeable material, in order to assure that the delivered fluid (and any solutes therein) traverse the entire length of the lumen. Outer lumen (52), in contrast, is formed of a semipermeable material to provide a microcatheter of the type described herein.

Optionally, and preferably, a microcatheter of this (or other suitable) type can be used to both monitor and treat the site, by the use of reservoir portions adapted for such use. For instance, apparatus (40) can be used to first monitor the site by sampling the interstitial fluid, since ischemia is generally associated with either increased pressure or a lowering of pH within the affected tissue. As seen in FIG. 5, a preferred monitoring reservoir can include a number of optional features, such as a chemical or metabolic (e.g., pH) indicator portion (56) and a pressure indicator (58).

In the event compartment syndrome is indicated, a new microcatheter/reservoir assembly can be positioned in the sheath in order to deliver a hyperosmolar solution and reduce pressure in the site. As seen in FIG. 9, therapeutic reservoir (60) is fabricated having an elastomeric outer balloon (62) and an impermeable elastomeric inner balloon (64) containing a hyperosmolar solution (66), which in turn optionally contains therapeutic agents. Positioned between balloons (62) and (64) is a fluid reservoir (68). Upon flow of solution (66) from the inner balloon, through the coaxial microcatheter, and back to fluid reservoir (68), the inner balloon is able to contract by virtue of its natural elasticity (and further deliver fluid via hydrostatic means) as the outer balloon expands to accommodate the increasing volume of recovered fluid. Optionally, and as shown in FIG. 9, the outer balloon also includes one or more needle ports (70) that permit the user to sample or remove the contents of the outer balloon (68).

Returning briefly to FIG. 8, there is shown an apparatus for use in by negative pressure. The apparatus (70) includes a manifold and fluid collecting reservoir (72) that is operably connected via conduit (74) to a source of negative pressure (not shown) and to a plurality of microcatheter or other recovery conduits. Preferably, the microcatheters are provided in the form of porous or open sheaths, such as the sheath shown in FIG. 7 with respect to the placement of microcatheter assemblies.

Turning next to FIGS. 10 through 13 there is shown preferred embodiments of an apparatus (80) for use in treating cerebral edema. Apparatus (80) includes a generally hollow and cylindrical rigid portion (82), which in turn is comprised of stepped down portions (84) and (86), for traversing the soft tissue and skull, respectively. Positioned within portion (82) is a telescoping portion (88), which in turn is dimensioned to retain a plurality of microcatheters (90). In use, rigid portion (82) is positioned through the surrounding tissue and within the skull, whereupon telescoping portion (88) is positioned into the brain to the desired point.

Figure 12:
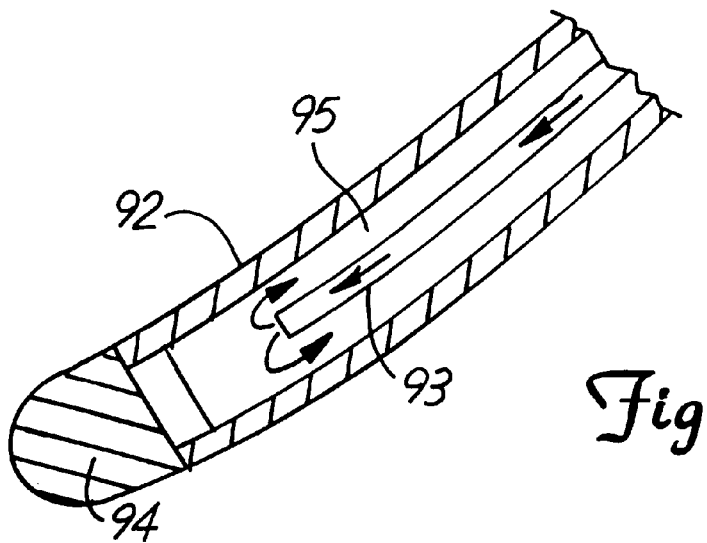
FIGS. 12 and 13 show alternative preferred embodiments of the microcatheter portion of the apparatus of FIG. 10.
Figure 13:
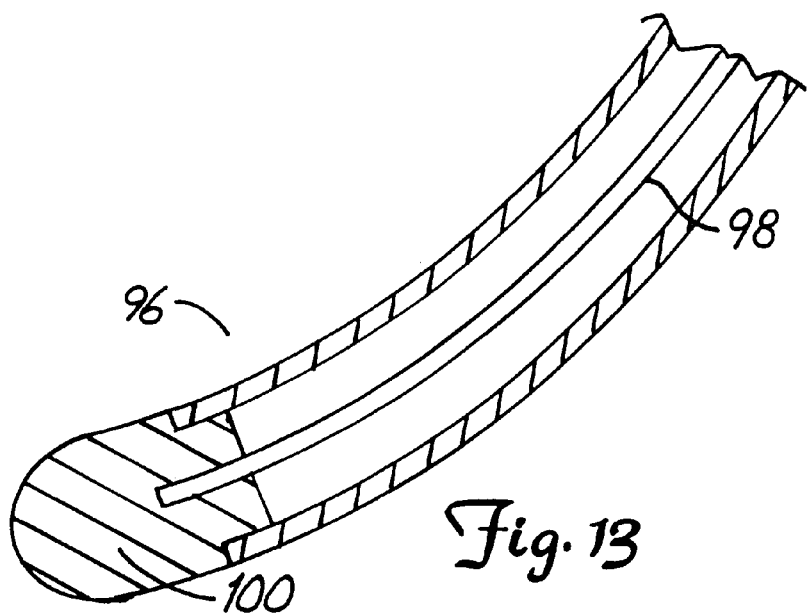

Once in place, microcatheter portions (90) are themselves positioned (e.g., splayed) from the distal end of telescoping portion (88) to their final position within the brain. The microcatheters, in turn, can be of any suitable type as described herein. FIG. 12, for instance, shows a preferred embodiment in which a coaxial recover microcatheter (92) is provided, having inner lumen (93) and outer microporous lumen (95), together with a solid polymeric tip (94), which is optionally fluted or otherwise shaped to facilitate placement. Such a microcathter can be used to deliver hyperosmolar solutions in the manner described above. FIG. 13 shows an alternative embodiment (96) in which one or more recovery microcatheters are used, having central guidewires (98) and solid polymeric tips (100) to facilitate placement and use.

Figure 14:
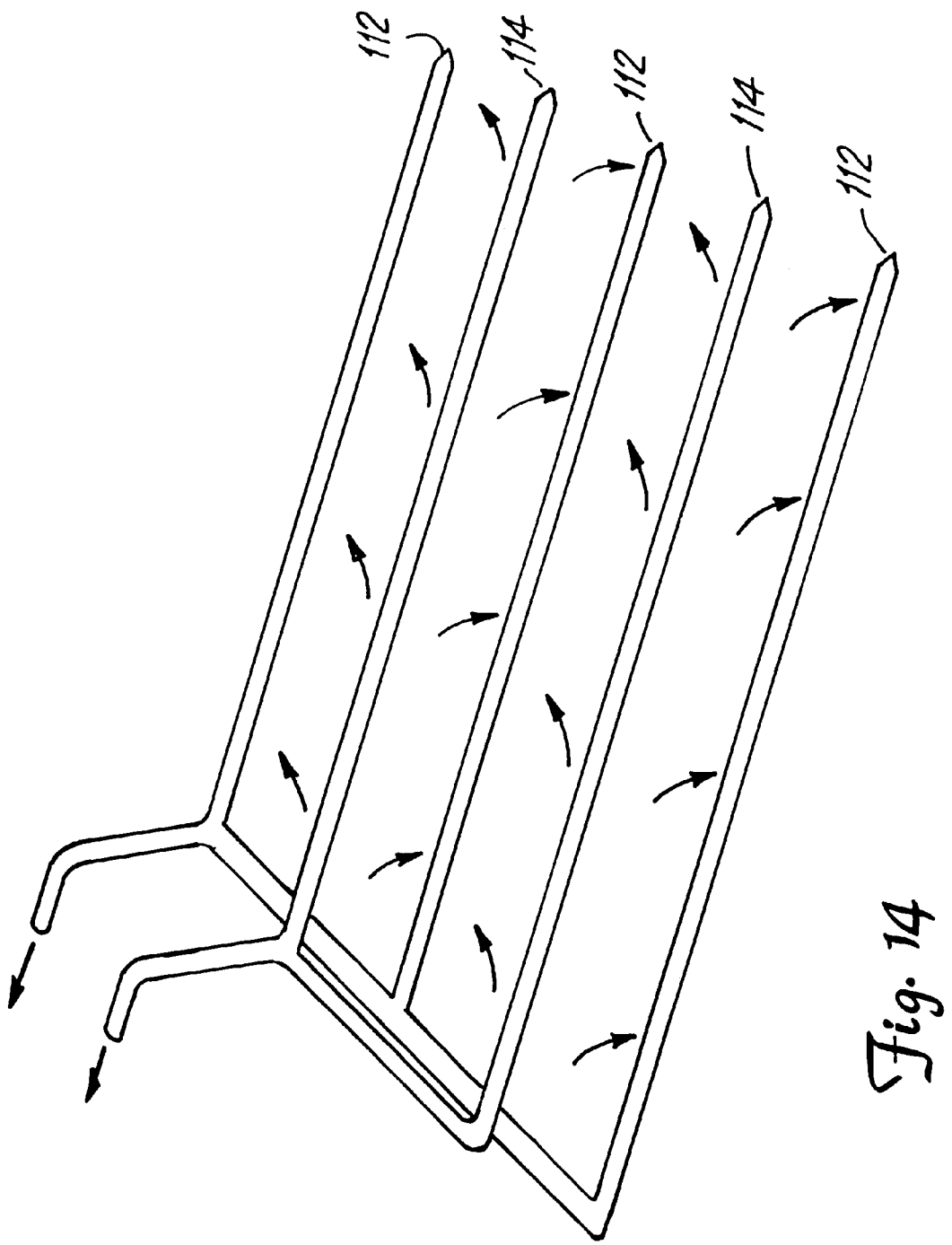
FIG. 14 shows a preferred two dimensional, dual catheter (delivery and recovery) apparatus for use in skin flap survival or subcutaneous augmentation.

FIGS. 14 through 17 show a variety of preferred embodiments of dual- and higher-catheter arrangements for both in vivo use, e.g., in the treatment of skin flaps and solid tumors, and for in vitro use, e.g., for tissue culture and regeneration. FIG. 14, for instance, shows a preferred embodiment of a dual catheter assembly (110) having a plurality of recovery catheters (112), connected to a recovery pump reservoir (not shown) laying in parallel to a plurality of delivery fibers (114), similarly connected to a delivery pump reservoir. The catheters themselves can take any suitable form, e.g., in the form of hollow (and optionally open ended) microporous catheters (of the type shown in FIG. 13, optionally having a central guide wire). Preferably, one or more of the delivery catheters is provided in the form of a coaxial catheter, of the type shown in FIG. 12, in order to facilitate the establishment of convective flow between delivery and recovery fibers by providing the flow of fluid in each in a single desired direction.

Figure 11:
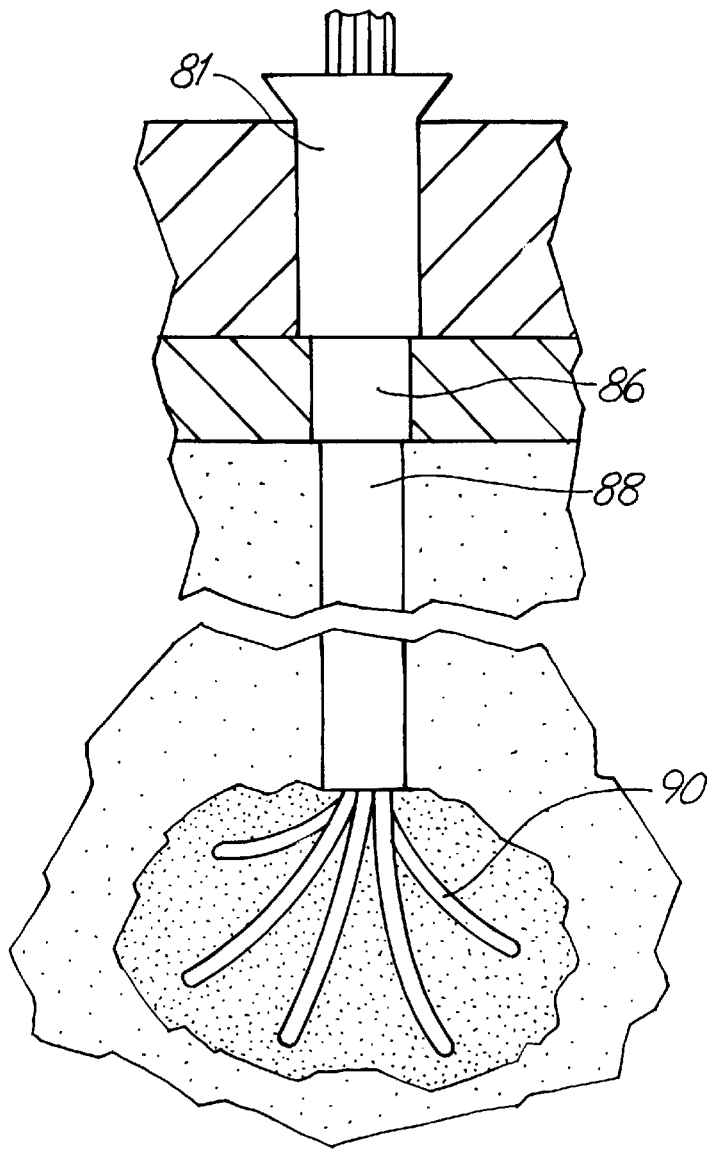
FIG. 11 shows the apparatus of FIG. 10 in position within the skull and brain.
Figure 15:
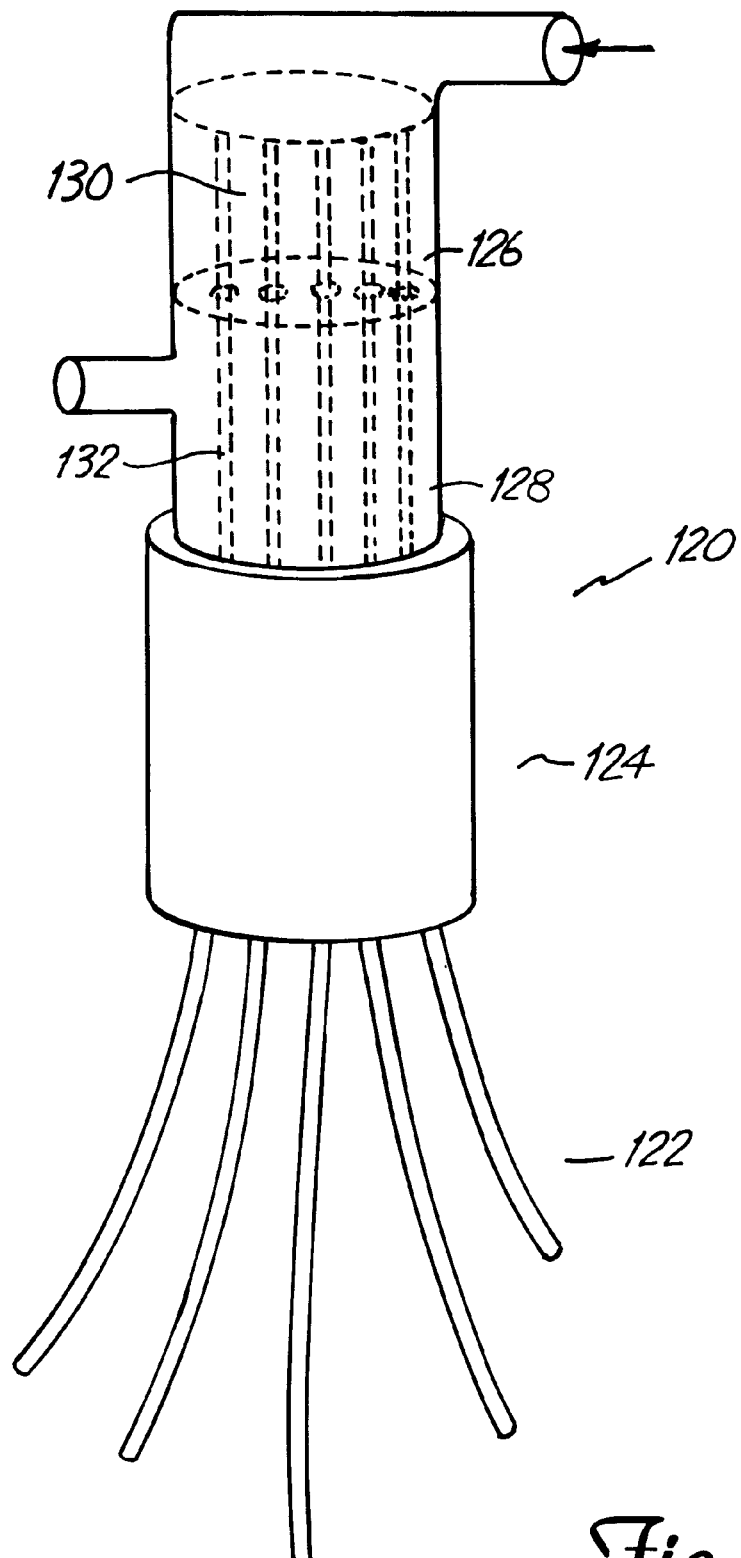
FIG. 15 shows a preferred fluid chamber configuration for embodiments such as that in FIG. 11, having a plurality of coaxial microcatheters.

FIG. 15, in turn, shows a representative apparatus (120) showing the relationship of delivered and recovered fluid chambers, e.g., for use in combination with a coaxial microcatheter assembly as shown in FIG. 11. Such an apparatus can be used for other applications as well, such as placement into tissue by use of A plurality of porous microcatheters (122), preferably of the coaxial type described herein, are positioned to splay out from the body (124). Body (124), in turn, supports fluid chambers (126) and (128) for containing, respectively, fluid for delivery and recovered fluid. The fluid delivery chamber (126) is itself shown as attachable to a pump reservoir (not shown) containing the fluid to be delivered. Fluid recovery chamber (128), in turn, is shown attachable to a reservoir (not shown) for containing or removing the recovered fluid. The interior passageways (130) of each catheter can be attached to a manifold positioned within fluid delivery chamber (126), while the exterior passagewayss are positioned within the fluid recovery chamber (128).

In use, the splayed coaxial microcatheters can be positioned with a suitable tissue or material and there used to both deliver fluid via the interior passageway, and recover fluid from the surrounding medium by means of the outer passageway, and semipermeable nature of the outer wall. Optionally, and preferably, microcatheters used in this invention can have regions of varying characteristics, including varying porosity, rigidity, and the like, for instance those that vary between sequential and adjacent, or suitably spaced, longitudinal sections, or in or any other suitable pattern. Such variations can be used, for instance, in a size exclusion fashion to improve or provide the ability to retain or permit the passage of solutes of varying sizes in a predetermined manner. Such variations can also be used to provide regions of greater rigidity or varying structure (e.g., fluted), in order facilitate their placement in tissue. Such variations can also include the incorporation of means (e.g., radioopaque materials) to facilitate the visualization of implanted catheters.

Figure 16:
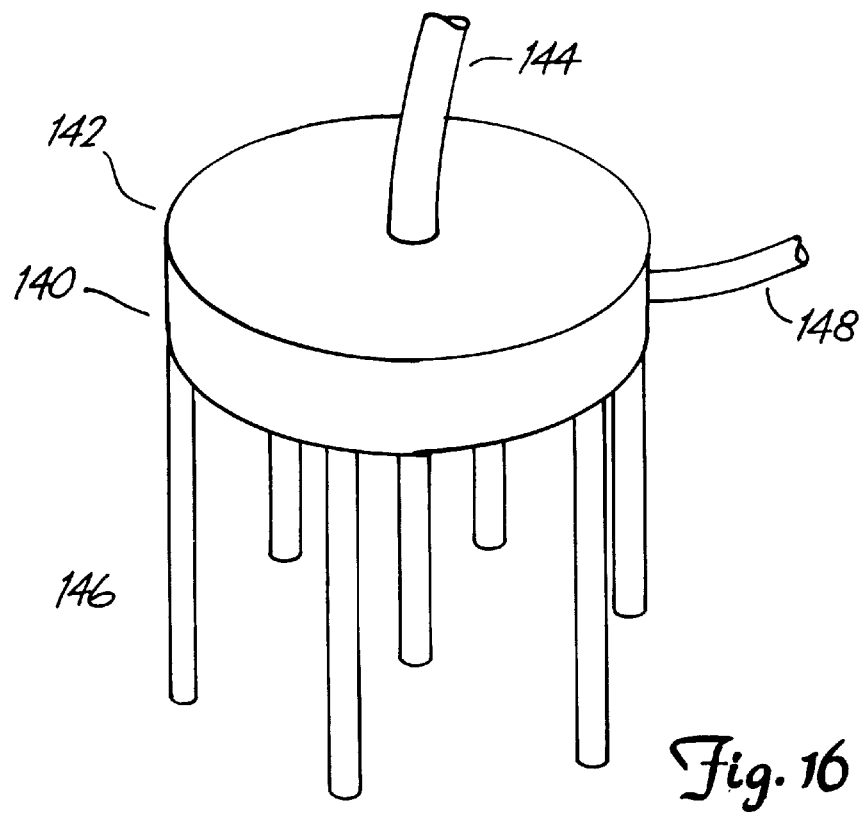
FIGS. 16 and 16A show side and top views of a preferred three dimensional dual catheter apparatus for use in treating intact tissues.
Figure 16A:
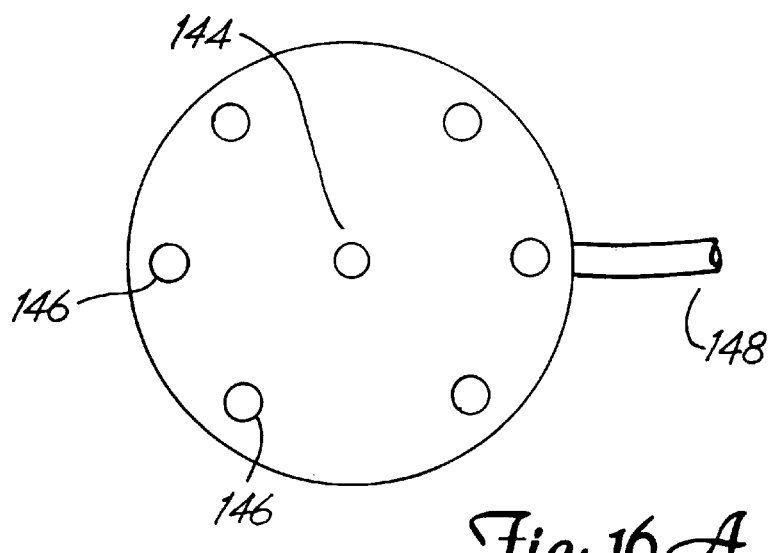

FIGS. 16 and 16A show a representative embodiment of an apparatus (140) of this invention for use in treating tissue. Disc portion (142) is used to retain one or more delivery conduits (144) as well as one or more (and preferably a plurality of) recovery conduits (146) in the form of microcatheters. The recovery microcatheters, in turn, can be connected to manifold arrangement (not shown, but preferably positioned within disc (142)), and can be finally removed via recovery conduit (148). FIG. 16A shows a top view of the apparatus of FIG. 16, showing a preferred arrangement in which a plurality recovery conduits (e.g., six, in order to provide a desired hexagonal configuration) are positioned in and equidistant fashion from a single delivery conduit.

In use, the apparatus of FIG. 16 is preferably positioned with its recovery microcatheters positioned within a desired site such as tissue, and the disc portion and/or delivery conduit positioned either within or outside the body. Such an embodiment is particularly well suited to treating three dimensional areas such as tumors, in order to both deliver fluid containing therapeutic agents and recover fluid from the site as well.

Figure 17:
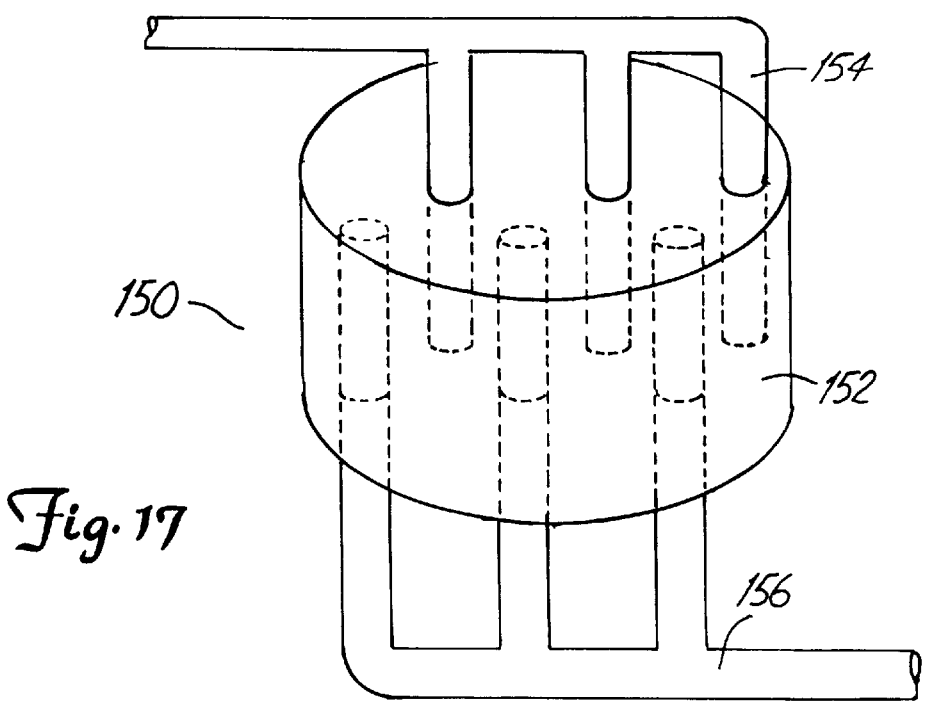
FIG. 17 shows a preferred three dimensional dual catheter apparatus for use in tissue culture and tissue engineering.

Finally, FIG. 17 shows a representative dual catheter embodiment for the use in tissue culture and tissue engineering. The apparatus (150) includes a block of material (152) suitable for providing a framework (e.g., cell scaffold) for the growth of cells or tissue. Examples of such materials include, for instance, hydroxyapatite, polymeric matrices, and biologically acceptable ceramics. Positioned within the block are one or more delivery microcatheters (154) and one or more recovery microcatheters (156). In use, the block can be seeded with cells and incubated under conditions suitable to facilitate the growth of such cells or tissue. In the course of incubation, the delivery and recovery systems can be employed to provide the cells with required nutrients and remove waste and other products. The cells can be incubated in vitro, or the apparatus can be implanted into the tissue with the catheters attached, and incubation can proceed in vivo. Once the cells or tissue have grown to a desired degree (e.g., confluence), a block that has been incubated in vitro can be implanted in the body as a tissue substitute. Optionally, and preferably the block is shaped (either prior to or after cell growth) for its intended purpose.

Pump reservoirs suitable for use in an apparatus in the present invention can take any suitable form, including those used externally from the body and those implanted within it. See, for example, "Primer: High-technology i.v. infusion devices", J. S. Kwan, *Amer. J Hosp. Pharm.* 46:320–335, (1989), the disclosure of which is incorporated herein by reference. Such infusion devices can be classified according to a number of criteria, including the use of pressure, the mechanism of operation peristaltic systems, syringe pumps, cassette systems, elastomeric reservoir, the frequency of delivery (e.g., continuous, intermittent multiple rate programmable, and those responsive to physiologic conditions or status), and whether they are intended for institutional or ambulatory settings.

An implantable apparatus of this invention, including pump component, can be implanted in any suitable manner, including intravenous, intra-arterial, epidural, subcutaneous, and intraperitoneal routes. Such an apparatus is effectively self-powered to deliver fluid in a desired manner (e.g., rate) over a desired period of time. When attached to a microcatheter, such pumps can be used for infusion or targeted delivery to any organ or tissue, including bone. Such pumps can be in the form of a continuous infusion pump that provides predictable delivery at controlled rate, and can be adapted to permit discontinuous or intermittent delivery. An example of a suitable pump is the pump system available under the tradename ALZET from Alza Corporation. Such pumps operate by virtue of an osmotic pressure difference between a compartment within the pump (referred to as the "salt sleeve") and the tissue environment into which the pump is implanted.

The high osmolality of the salt sleeve causes water to flux into the pump through an outer, semipermeable membrane. As the water enters, it compresses the reservoir, displacing the solution from the reservoir at a controlled, predetermined rate. The rate of solution delivery is controlled by the rate at which water enters the semipermeable membrane and compresses the reservoir. The volume rate delivery of such a pump can be fixed during manufacture. Accordingly, the rate of delivery of any therapeutic or other agent that contained within the reservoir can be adjusted by varying its concentration in that solution.

Such pumps include, from the interior outwardly, a reservoir having a delivery portal and being surrounded by an impermeable reservoir wall, which in turn is surrounded by an osmotic agent and in turn a semipermeable membrane to the aqueous environment. In their intended application, a protein solution is provided in the reservoir to be gradually released through the delivery portal by the pressure of the solution containing osmotic agent as it takes up liquid and swells. Optionally, such pumps can include the use of accessory components, such as infusion kits (catheters for attachment to the delivery portal) to target the delivery to particular locations remote from the pump itself.

The apparatus of this invention can be provided in the form of one or more kits, including a kit in which an apparatus is provided in combination with (e.g., prefilled with) one or more solutions (e.g., of the types described herein) in the pump reservoir, and a kit in which one or more apparatuses are provided together (e.g., the monitoring and therapeutic apparatuses described with respect to compartment syndrome), optionally in combination with a delivery sheath and/or an assembly for removing interstitial fluid (e.g., as shown in FIG. 8). In each such kit, the relative amounts of materials and/or dimensions of components can be predetermined and related for application to a particular site or condition.

Suitable materials for use as hollow fibers of the present invention provide an optimal combination of such properties as mass transfer properties, biocompatability, surface-to-volume ratio, processability, hydrophobicity/hydrophilicity, strength, transport rate, and porosity. Examples of suitable hollow fibers are described, for instance, I. Cabasso, "Hollow-Fiber Membranes", pp 598–599 in *Kirk Othmer Concise Encyclopedia of Chemical Technology.*

The dimensions of a hollow fiber will depend largely on the intended use of the apparatus. In a number of preferred embodiments, a hollow fiber will be provided in the form of a capillary having an outer diameter of less than about one centimeter, and preferably less than about three millimeter, and whose outer, tissue contacting, wall functions as a semipermeable membrane. These fibers can be used singly or can be grouped into bundles, e.g. containing several hundred or several thousand. In most cases, a hollow fiber will be used as a cylindrical membrane in a manner that permits selective exchange of materials across its walls. In some cases, however, the fiber will optionally (or also) be used as a 'container' to effect the controlled release of materials from the fiber, or as a 'reactor' to chemically modify a permeant as it diffuses through a chemically activated wall.

Hollow fibers of this invention can therefore be characterized as either being 'open', in which gas or liquid permeates across the fiber wall, while flow of the lumen medium is not restricted, or as being "loaded" such that the lumen is itself filled with an immobilized solid or liquid.

Microcatheters can be prepared in any suitable manner, e.g., by microperforating an otherwise intact capillary or by spinning hollow fiber membranes from natural or synthetic polymers. Such fibers can be formed having any desired characteristics, e.g., isotropic (dense or porous) and anisotropic (assymetric). Examples of suitable materials for use as microcatheters of this invention include, but are not limited to, microinfusion tubing such as polyethylene tubing available from Clay Adams under the designations PE-10 (0.28 mm/0.61 mm, inner and outer diameters), PE-20 (0.38 mm/1.09 mm), PE-50 (0.58 mm/0.965 mm) and PE-90 (0.86 mm/1.27 mm). Such tubing can be microperforated by any suitable means, such as lasers and the like. Other examples of suitable materials include microdialysis fibers such as those identified in the following table:

| Types | Manufacturer | Catalog No. | Interior Diameter (um) | Wall Thickness (um) | Ultrafiltration Rate(mL/min)/ Surface Area (sq. meter) |
| --- | --- | --- | --- | --- | --- |
| Cuprophan | Baxter Haemodialysis Products | unknown | 200 | 8 | unknown |
| Hemophan FoCus 160-H | Baxter Haemodialysis Products | unknown | 200 | 8 | unknown |
| Spectra/Por Regenerated Cellulose | Spectrum 23022 La Cadena Drive, Suite #100 Laguna Hills, Ca. 92653 | #132–200 through 132–313 membrane types vary according to m.w., volume, pH, and chemical compatibility | 200 | 10–20 | 25–15 |
| Cellulose Triacetate CT-190 | Baxter Haemodialysis Products | CT-190 series #5M1546 CT-110–190 also available | 200 | unknown | unknown |
| Cellulose Acetate CA-170 | Baxter Haemodialysis Products | CA-170 series #5M–1735 CA-150-CA-170 series also available | unknown | unknown | unknown |
| Polysulfone Hemoflow F-60A High Flux | Fresenius | F60 series #0500136A F3-6,8, 40–80 series also available | 200 | 40 | 40/1.3 |
| Polyacrylo-nitrile (PAN) | Gambro-Health | | unknown | unknown | unknown |

The method and apparatus of this invention can be applied to a number of clinical conditions, including: 1) conditions such as reperftision injury or osteoradionecrosis, where the microcirculation is disrupted and thus the delivery of blood-borne agents is impaired, 2) conditions where tissue levels are inadequate because there is a systemic toxicity of agents such as antibiotics or antimetabolytes, and 3) conditions in which large, poorly diffusible molecules (antibodies, growth factors, enzymes, and genetic vectors) must be delivered to the interstitium.

In turn, the appartus of this invention can be used for a variety of applications, including edema therapy, e.g., by hydrostatic or osmolar forces, in sites such as skin flap survival, compartment syndrome, cerebral edema, stroke and ischemic heart disease. Similarly, the apparatus can be used for interstitial therapy, e.g., by diffusional or hydrostatic forces, in bone microdialysis for osteoporosis, to deliver agents directly to bone, for autologous transdialysis, for interpositional bone grafts, in normal adjacent bone to dialyze growth factors, for growth factors that diffluse out in graft, and for skin flaps or grafts. In yet another embodiment, the apparatus can be used for bone marrow chemoprotection, e.g., by placing the catheter into bone marrow, to increase perfusion pressure during intravenous infusion, or to perfuse with cell culture media The method and apparatus of the present invention allows interstitial delivery and/or removal of solvent and/or solute in finite tissue spaces, without reliance on an intact microcirculatory system. Specific immediate applications include the treatment of compartment syndrome and cerebral edema, prevention of tissue necrosis of skin flaps and grafts, and infusion of large molecules (immunoglobulins or genetic vectors), antibiotics, growth factors, and chemotherapeutic agents to a specific site. Other uses include site specific treatment of osteoporosis (i.e., femoral neck), protection of bone marrow spaces during infusion of chemotherapy, and development and implantation of large three dimensional bone grafts based on a hydroxyapatite scaffolding.

Yet other uses include tissue engineering of bone, cartilage, and soft tissue implants. An engineered block as described herein, for a can be fabricated in a form that can be attached to a prosthetic implant and the combination implanted into the body. For instance, a block can be engineered as a bone replacement and attached to an other prosthetic component and the combination implanted with the engineered portion serving as the interface between the implant and the body.

A number of other conditions that rely on circulation can benefit as well from application of the present method and apparatus, including solid tumor cancer treatment, heart disease, and liver failure. With regard to cancer, the ability to treat solid tumors by chemotherapy poses at least two challenges. The first challenge arises by virtue of the poor circulation that exists in older, more central areas of many tumors, which in turn means that agents administered systematically will not penetrate well or kill all tumor cells. Second, are problems having to do with the inherent toxicity of many, or most, chemotherapeutic agents. Although such agents are generally intended to cause cellular injury, their effect is desired only on tumor cells and not in healthy host tissues. Both of these problems can be exacerbated by poorly perfused central tumor cells, which will not effectively take up the chemotherapy. This, in turn, requires an increased dose and greater collateral cellular damage. The method and apparatus of this invention can be used to provide site-specific delivery of chemotherapeutic agents, including for agents having particular toxicity. Preferably, an apparatus for treating cancer will be in a dual catheter arrangement as described herein, with the conduit and active portion of the microexchange catheters customized to the location and size of the tumor.

In the treatment of heart disease there has been considerable interest recently in laser revascularization of the myocardium in patients having coronary artery disease. The laser addresses microcirculatory impairment. A large part of the success of the procedure has to do with draining extracellular fluid. We have shown in ischemic tissue of skin flaps, interstitial osmolarity increases along with the edema, so a solute load on the interstitial space is an important part of ischemic tissue reperfusion. Microdialysis catheters have been able to remove a hypertonic effluent from skin flaps, thereby not only reducing edema, but reducing solute load of the interstitial space. Microcatheters of an apparatus of this invention can be placed with minimal exposure or morbidity into the myocardium, producing the same benefits of the laser treatment but with even lower cost and morbidity. A preferred microcatheter apparatus of this invention, for use in treating the heart, is similar to that described above with respect to cerebral edema (both for fluid removal after ischemia), provided that the heart apparatus would preferably employ a small pliable connection tubing such as silicon to prevent tissue damage while the heart is beating.

Finally, liver failure is not a common problem, but is a lethal condition. Treatment options are limited. Liver transplantation is a morbid operation and donors are limited. There are commercial entities pursuing the development of bioartificial livers, which have been shown to be technically feasible, but are limited to extracorporeal use. The method and apparatus of the present invention, however, can be used to create an implantable artificial liver. The technical challenge to this endeavor is having sufficient vascularity of the implant to allow meaningful perfusion of hepatocytes. It is conceivable that microdialysis fibers, angiogenic growth factors, and actual vascular anastomoses to cultured vessels will make an implantable liver possible. A preferred apparatus for treating the liver will be in the form of a three-dimensional apparatus as described above in the context of tissue engineering, preferably also including the use of resorbable scaffoldling, such as resorbable hydroxyapatite. Other forms of organogenesis, such as the growth of islet cells for diabetics, will be made possible as well.

What is claimed is:

1. An apparatus for performing site specific microtherapy comprising a pump reservoir and one or more microcatheters dimensioned to be positioned within a tissue site for selectively removing fluids by microdialysis from the tissue site, the microcatheter(s) being adapted for fluid communication with the pump reservoir to effect the recovery of fluid, the apparatus further comprising a delivery sheath adapted to be positioned into the tissue site, the microcatheter assembly adapted to be positioned within the delivery sheath, the delivery sheath having walls sufficiently permeable to permit a desired flow of fluids between the tissue and the microcatheter assembly in the course of microdialysis.

2. A kit comprising an apparatus according to claim 1 wherein the microcatheter assembly comprises a plurality of microcatheters adapted to be positioned within the delivery sheath.

3. A kit according to claim 2 wherein the microcatheter assembly is adapted to perform microdialysis based on size exclusion in order to remove tissue fluids and solutes based on solute size.

4. A kit according to claim 3 wherein the microcatheter assembly comprises a plurality of microcatheters, each in the form of a capillary tube having a lumen and semipermeable wall.

5. A kit according to claim 2 wherein the apparatus provides a plurality of fluid passageways.

6. A kit according to claim 5 wherein the passageways comprise a passageway adapted to deliver a solution to the tissue and a second passageway adapted to recover fluid from the tissue.

7. A kit according to claim 2 wherein the apparatus is adapted to permit physiologic parameters to be simultaneously monitored.

8. A kit according to claim 2 wherein the apparatus is adapted for use in treating cerebral edema.

9. An apparatus according to claim 1 wherein the microcatheter assembly is adapted to perform microdialysis based on size exclusion in order to remove tissue fluids and solutes based on solute size.

10. An apparatus according to claim 9 wherein the microcatheter assembly comprises a plurality of microcatheters, each in the form of a capillary tube having a lumen and semipermeable wall.

11. An apparatus according to claim 1 wherein the apparatus provides a plurality of fluid passageways.

12. An apparatus according to claim 11 wherein the passageways comprise a passageway adapted to deliver a solution to the tissue and a second passageway adapted to recover fluid from the tissue.

13. An apparatus according to claim 1 wherein the apparatus is adapted to permit physiologic parameters to be simultaneously monitored.

14. An apparatus according to claim 1 wherein the apparatus is adapted for use in treating cerebral edema.

15. A method of performing site specific microdialysis, the method comprising the steps of:

a) providing an apparatus comprising one or more microcatheters dimensioned to be positioned within a tissue site for selectively removing fluids by microdialysis from the tissue site, the microcatheter(s) being adapted for fluid communication with a reservoir component for the recovery of fluid, the apparatus further comprising a delivery sheath adapted to be positioned into the tissue site, the microcatheter assembly adapted to be positioned within the delivery sheath, the delivery sheath having walls sufficiently permeable to permit a desired flow of fluids between the tissue and the microcatheter assembly in the course of microdialysis b) positioning the delivery sheath and microcatheter assembly of the apparatus within a tissue site, and c) employing the apparatus to selectively remove fluid by microdialysis from the tissue site.

16. A method according to claim 15 wherein the microcatheter assembly is adapted to perform microdialysis based on size exclusion in order to remove tissue fluids and solutes based on solute size.

17. A method according to claim 16 wherein the microcatheter assembly comprises a plurality of microcatheters, each in the form of a capillary tube having a lumen and semipermeable wall.

18. A method according to claim 15 wherein the apparatus provides a plurality of fluid passageways.

19. A method according to claim 18 wherein the passageways comprise a passageway adapted to deliver a solution to the tissue and a second passageway adapted to recover fluid from the tissue.

20. A method according to claim 15 wherein the apparatus is adapted to permit physiologic parameters to be simultaneously monitored.

21. A method according to claim 15 wherein the apparatus is adapted for use in treating cerebral edema.

* * * * *